(12) United States Patent
Kajanto et al.

(10) Patent No.: US 10,822,743 B2
(45) Date of Patent: *Nov. 3, 2020

(54) PROCESS FOR PRODUCING A NANOFIBRILLAR CELLULOSE HYDROGEL

(71) Applicant: UPM-KYMMENE CORPORATION, Helsinki (FI)

(72) Inventors: Isko Kajanto, Espoo (FI); Markus Nuopponen, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/578,778

(22) PCT Filed: Jun. 2, 2016

(86) PCT No.: PCT/FI2016/050393
§ 371 (c)(1),
(2) Date: Dec. 1, 2017

(87) PCT Pub. No.: WO2016/193548
PCT Pub. Date: Dec. 8, 2016

(65) Prior Publication Data
US 2018/0179703 A1    Jun. 28, 2018

(30) Foreign Application Priority Data
Jun. 4, 2015 (FI) ..................... 20155425

(51) Int. Cl.
| | | |
|---|---|---|
| D21B 1/30 | (2006.01) | |
| C08B 15/04 | (2006.01) | |
| A61K 8/04 | (2006.01) | |
| A61K 8/73 | (2006.01) | |
| A61K 9/06 | (2006.01) | |
| A61K 31/717 | (2006.01) | |
| A61Q 19/00 | (2006.01) | |
| C12N 5/00 | (2006.01) | |
| D21C 9/02 | (2006.01) | |
| D21C 9/10 | (2006.01) | |

(52) U.S. Cl.
CPC .............. *D21B 1/30* (2013.01); *A61K 8/042* (2013.01); *A61K 8/731* (2013.01); *A61K 9/06* (2013.01); *A61K 31/717* (2013.01); *A61Q 19/00* (2013.01); *C08B 15/04* (2013.01); *C12N 5/0018* (2013.01); *D21C 9/02* (2013.01); *D21C 9/10* (2013.01); *A61K 2800/10* (2013.01); *A61K 2800/81* (2013.01)

(58) Field of Classification Search
None
See application file for complete search history.

(56) References Cited

U.S. PATENT DOCUMENTS

| | | | | |
|---|---|---|---|---|
| 4,302,252 A | * | 11/1981 | Turbak | C08B 1/003 106/200.2 |
| 5,858,392 A | | 1/1999 | Dumitriu | |
| 7,381,328 B2 | * | 6/2008 | Schrive | B01D 21/0009 210/243 |
| 2014/0010790 A1 | * | 1/2014 | Yliperttula | A61K 9/06 424/93.7 |
| 2014/0349377 A1 | * | 11/2014 | Lauraeus | C12N 1/20 435/253.6 |
| 2015/0010980 A1 | | 1/2015 | Lauraeus | |

FOREIGN PATENT DOCUMENTS

| | | |
|---|---|---|
| CN | 104105827 A | 10/2014 |
| JP | 5727657 B1 | 6/2015 |
| WO | 2012056109 A2 | 5/2012 |
| WO | 2013072563 A1 | 5/2013 |
| WO | 2013093197 A1 | 6/2013 |
| WO | WO 2013/117823 | 8/2013 |
| WO | 2014128354 A1 | 2/2014 |
| WO | 2014049204 A1 | 4/2014 |

OTHER PUBLICATIONS

Krafft, M.P., Strasbourgh's Sofft Team—Soft function systems self-assembled from perfluoroalkylated molecular components, Journal of Fluorine Chemistry, vol. 134 (2012), p. 90-102.
Avestic Inc., High Pressure homogenizers, Internet publication, http://www.faucitano.it/files/catalog/Produkt%20Brochuere2.pdf, Published Nov. 3, 2011.
Madhushree Bhattacharya, et al., Nanofibrillar cellulose hydrogel promotes three-dimensional liver cell culture, Journal of Controlled Release, 164, 2012, 291-298.
International Search Report from International Application No. PCT/FI2016/050393 dated Aug. 31, 2016.
Search Report from Finnish Patent Application No. 20155425 dated Oct. 2, 2015.
Enzyme Technology, High pressure homogenisers, http://www1.lsbu.ac.uk/water/enztech/pressurec.html, retrieved Jan. 8, 2015.
Dong, M., "Food Microbiology [First Edition]," China Light Industry Press, p. 297 (2011).

(Continued)

*Primary Examiner* — Dale R Miller
(74) *Attorney, Agent, or Firm* — Nixon Peabody LLP

(57) ABSTRACT

A process for producing a nanofibrillar cellulose hydrogel comprises obtaining bleached cellulose pulp fibers and providing an aqueous suspension thereof; and subjecting the cellulose pulp fibers in the aqueous suspension to at least 2 cycles of high pressure mechanical disintegration to obtain a nanofibrillar cellulose hydrogel and thereby reducing the number of viable microorganisms present in the suspension by a factor of at least $10^2$; wherein all steps of the process after obtaining the bleached cellulose pulp fibers are performed under conditions of ISO 8 of ISO 14644-1 cleanroom standards or stricter. A nanofibrillar cellulose hydrogel, a system for producing the same and the use of a disintegrating apparatus are also disclosed.

18 Claims, 1 Drawing Sheet

(56) References Cited

OTHER PUBLICATIONS

Sun, Y., "Preparation of HPMC Hydrogel Microspheres and Its Application in Drug Release," China Full-text Database of Excellent Master Degree Thesis, Engineering Science and Technology I, Issue S2, p. B016-328 (2011).

Du, Z., "Pathogen Biology and Immunology [First Edition]," China Medicine Science Press, p. 143 (2012).

He, C., "Medical Microbiology Experiment Technology [First Edition]," pp. 51-52 (1981).

Chinese Office Action in Chinese Patent Application No. CN 201680031425.6, dated Mar. 18, 2020 (10 pages).

* cited by examiner

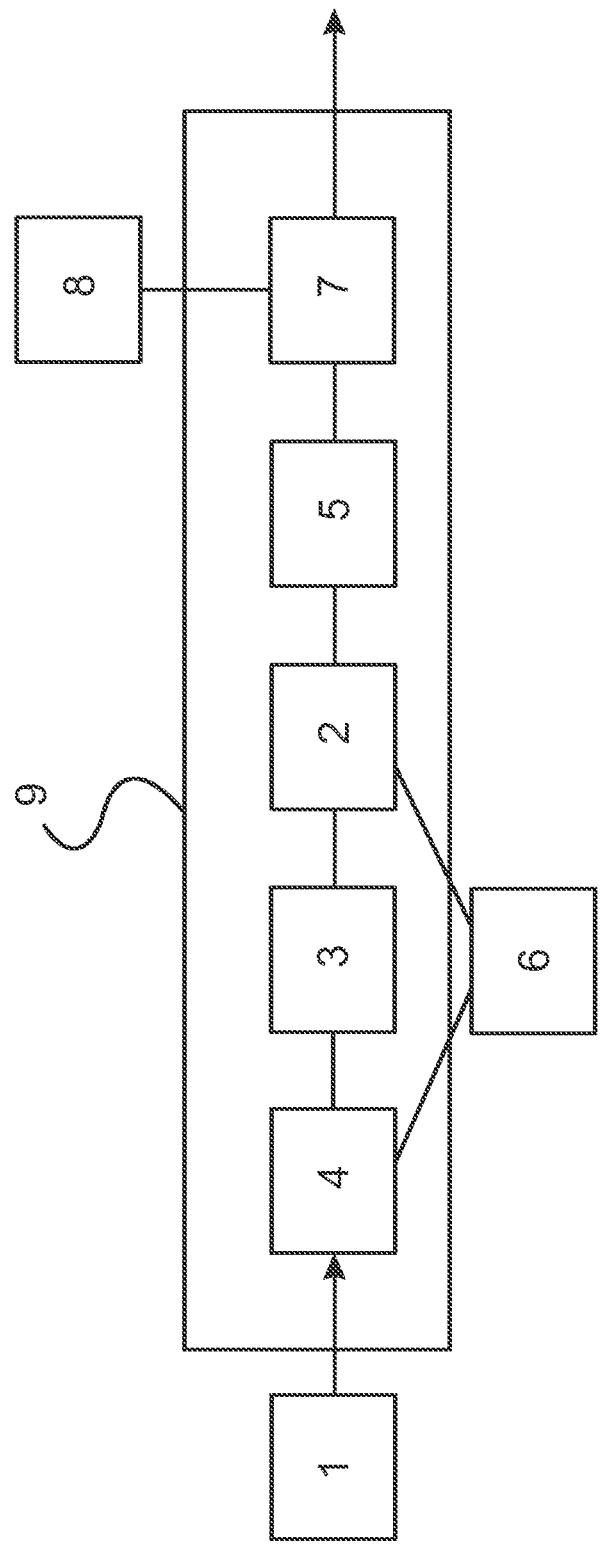

PROCESS FOR PRODUCING A NANOFIBRILLAR CELLULOSE HYDROGEL

CROSS-REFERENCE TO RELATED APPLICATIONS

This application is a U.S. National Stage Application of International Application No. PCT/FI2016/050393, filed on Jun. 2, 2016, which claims priority to Finnish Patent Application No. 20155425, filed on Jun. 4, 2015, both of which are incorporated by reference herein in their entireties.

FIELD OF THE INVENTION

The invention relates to a process for producing a nanofibrillar cellulose hydrogel, a nanofibrillar cellulose hydrogel, its uses, a system for producing the same and a use of a high pressure mechanical disintegration apparatus.

BACKGROUND

Nanofibrillar cellulose hydrogel has found use in various applications, such as in cosmetics, pharmaceuticals and as a growth medium for cell culture. However, such uses typically require that the hydrogel is aseptic or sterile. Yet other properties of the hydrogel should not be affected by sterilization.

Generally, sterilization efficiency is defined as the ability to remove or destroy all forms of microbial life, including viruses, bacteria and fungi, as vegetative forms or spores. However, since absolute sterility cannot be verified, a statistical definition of sterility is used in practice. For instance, the security assurance level (SAL) is defined as "the probability of a single viable micro-organism occurring in or on a product after sterilization". The worldwide accepted definition of sterility of medical devices is defined as the chance of finding a viable organism in or on a medical device to be at most 1 in 1000000 or a SAL of at most $10^{-6}$.

The number of viable micro-organisms in nanofibrillar cellulose hydrogel can be reduced or eliminated e.g. by subjecting the hydrogel to overkill autoclaving for 20 minutes at a temperature of 121° C. Such overkill autoclaving may be quite effective, as the number of viable microorganisms in the nanofibrillar cellulose hydrogel may typically be reduced by a factor of at least $10^{12}$. However, overkill autoclaving also has some drawbacks, as it may adversely affect the properties of the hydrogel. It may also be labour-intensive and may have to be done batchwise. Further, overkill autoclaving is typically conducted with the caps of the autoclaving vessels being loosened to prevent boilover and breakage, and there may be a need to tighten the caps after the containers and the contents have cooled down, as the vacuum resulting from the cooling of the steam in the vessel may cause the cap or vessel to shatter, thereby causing a contamination risk.

The inventors have therefore recognized the need for a process of producing nanofibrillar cellulose hydrogel such that it is suitable for further applications.

SUMMARY

The process is characterized by what is presented in claim 1.

The nanofibrillar cellulose hydrogel is characterized by what is presented in claim 17.

The nanofibrillar cellulose hydrogel for use in therapy is characterized by what is presented in claim 23.

The use of the nanofibrillar cellulose hydrogel is characterized by what is presented in claims 24 and 25.

The system for producing a nanofibrillar cellulose hydrogel is characterized by what is presented in claim 26.

The use of a high pressure mechanical disintegration apparatus in the production of a nanofibrillar cellulose hydrogel is characterized by what is presented in claim 31.

BRIEF DESCRIPTION OF THE DRAWINGS

The accompanying drawings, which are included to provide a further understanding of the invention and constitute a part of this specification, illustrate embodiments and together with the description help to explain the principles of the invention. In the drawings:

FIG. 1 illustrates a system according to one embodiment for producing a nanofibrillar cellulose hydrogel.

DETAILED DESCRIPTION

A process for producing a nanofibrillar cellulose hydrogel comprises obtaining bleached cellulose pulp fibers and providing an aqueous suspension thereof; and subjecting the cellulose pulp fibers in the aqueous suspension to at least 2 cycles of high pressure mechanical disintegration to obtain a nanofibrillar cellulose hydrogel and thereby reducing the number of viable microorganisms present in the suspension by a factor of at least $10^2$;

wherein all steps of the process after obtaining the bleached cellulose pulp fibers are performed under conditions of ISO 8 of ISO 14644-1 cleanroom standards or stricter.

The expression "nanofibrillar cellulose" or "NFC" may be understood in this specification, unless otherwise stated, as referring to a collection of isolated cellulose nanofibrils (CNF) and/or nanofibril bundles derived from a cellulose-based raw material.

Nanofibrils typically have a high aspect ratio. The length might exceed one micrometer while the diameter is typically below 200 nm. The smallest nanofibrils are similar to so called elementary fibrils, which are typically approx. 2-12 nm in diameter. The dimensions of the fibrils or fibril bundles are dependent on the raw material and the disintegration method. The number average diameter of nanofibrillar cellulose may vary from 1 to 100 nm, such as from 1 to 50 nm, or from 2 to 15 nm. Typically, native (non-derivatized) grades have larger diameters and wider fibril size distribution while derivatized (e.g. anionic, cationic) grades have smaller diameters and narrower size distributions. The diameter of a fibril may be determined with several techniques, such as by using a microscope. Fibril thickness and width distribution may be measured by image analysis of images from a field emission scanning electron microscope (FE-SEM), a transmission electron microscope (TEM), such as a cryogenic transmission electron microscope (cryo-TEM), or an atomic force microscope (AFM). In general, AFM and TEM suit NFC grades with narrow fibril diameter distribution best.

Cellulose pulp fibers may be obtained from a cellulose-based raw material. The expression "cellulose-based raw material" may be understood in this specification, unless otherwise stated, as referring to any raw material source that contains cellulose and from which cellulose pulp fibers, and subsequently nanofibrillar cellulose, can be produced.

The cellulose-based fiber material may, in principle, be based on any plant material that contains cellulose. The plant material may be wood. The wood may be from a softwood tree such as spruce, pine, fir, larch, douglas-fir or hemlock, or from a hardwood tree such as birch, aspen, poplar, alder, *eucalyptus* or acacia, or from a mixture of softwoods and hardwoods. Non-wood material may be derived from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. Depending on the raw material source, e.g. hardwood (HW) vs. softwood (SW) pulp, different polysaccharide compositions may exist in the final NFC product. The nanofibrillar celluloses may contain hemicelluloses and lignin in varying amounts, depending on plant source and pulping conditions. For example, bleached birch pulp has a high xylose content (25% by weight) and a negligible lignin content. The nanofibrillar celluloses are always complex mixtures of different polysaccharide structures.

The cellulose-based fiber material may be formed by isolating cellulose fibers from a raw material that contains cellulose by chemical, mechanical, thermo-mechanical, or chemi-thermo-mechanical pulping processes, for example kraft pulping, sulfate pulping, soda pulping, organosolv pulping, and by conventional bleaching processes. The cellulose-based fiber material may not contain substantial amounts of lignin, or it may contain only traces of lignin or non-detectable amounts of lignin. Thus also the NFC may be essentially lignin-free.

Nanofibrillar cellulose is characterized by very high water retention values, a high degree of chemical accessibility and the ability to form stable gels, hydrogels, in water or other polar solvents. A nanofibrillar cellulose product is typically a dense network of highly fibrillated cellulose. In an aqueous environment, a dispersion of cellulose nanofibers forms a viscoelastic hydrogel network. The hydrogel is formed at relatively low concentrations, for example 0.05-0.2% (w/w), of dispersed and hydrated entangled fibrils.

The cellulose pulp comprises both crystalline and amorphous regions in the cellulose. The crystallinity of the cellulose pulp used as the starting material may be at least 50%. Suitably the crystallinity of the cellulose pulp is at least 55%, such as at least 60%, or at least 65%, or at least 70%. Examples of suitable crystallinity values of the NFC include from 50 to 85%, such as from 60% to 80%, or from 65 to 75%. The NFC consists essentially of cellulose I.

The expression "hydrogel" or "nanofibrillar cellulose hydrogel" may be understood in this specification, unless otherwise stated, as referring to an aqueous dispersion of nanofibrillar cellulose having a continuous or discontinuous gel structure. The term "discontinuous" gel structure may be understood as referring to a continuous gel, which is broken into pieces of continuous gel structure. The hydrogel can be formed by combining nanofibrillar cellulose with e.g. water, buffer solution, cell culture medium or any other aqueous solution optionally supplemented with additives. The storage modulus (G') value of the hydrogel of nanofibrillar cellulose is greater than its loss modulus (G") value, the ratio of these, the loss tangent (G"/G'), being less than 1 at least up to strain value 10%.

The viscoelastic properties storage modulus G', loss modulus G" and loss tangent (G"/G') of the NFC hydrogels may be determined with the frequency sweep in dynamic oscillation mode of the rheometer (strain 1% and 10%, frequency 0.1-100, temperature 25° C., pH 7.0). The stress sweep is measured in a shear stress range of 0.001-100 Pa at the frequency 0.1 Hz, at 25° C., pH 7. For characterizing the gel forming capacity of a nanofibrillar cellulose grade the measurement is performed in 0.5 wt %, 1% strain, frequency of 0.1 Hz. For determining whether a certain material is a gel, i.e. whether its loss tangent is <1, the measurement is performed in the same way except in the consistency of the material (i.e. the material is not diluted prior to measurement). The storage modulus of oxidized nanofibrillar cellulose hydrogels may vary from 1 to 100 Pa, and typically the storage modulus varies from 2 to 50 Pa, or 5 to 20 Pa, in water at 0.5 wt % concentration. The storage modulus of native nanofibrillar cellulose hydrogels may vary from 0.3 to 20 Pa. Typically the storage modulus varies from 1 to 10 Pa, or 1 to 5 Pa, in water at 0.5 wt % concentration.

The process may be a process for producing a sterile or essentially sterile nanofibrillar cellulose hydrogel.

The expression "sterile" may be understood in this specification, unless otherwise stated, to refer to a nanofibrillar cellulose hydrogel or other substance, material, composition or component that is essentially free of viable micro-organisms. Because it is, in practice, very difficult to demonstrate that the nanofibrillar cellulose hydrogel would in fact be absolutely sterile, the sterility may be defined on the basis of measurement of the number of viable micro-organisms present in the nanofibrillar cellulose hydrogel by measuring the number of colony forming units.

In the context of this specification, the term "colony forming unit" or "CFU" should, as it is commonly used in microbiology, be understood as a measure or estimate of the number of viable micro-organisms in a sample. It corresponds to the formation of a single macroscopic colony after the introduction of one or more micro-organisms to microbiological growth media. Means and methods for estimating colony forming units are well known in microbiology. The presence of viable micro-organisms in the nanofibrillar cellulose hydrogel can be determined by culturing on a growth medium. Several protocols for determining the number of colony forming units are available.

In an embodiment, the number of colony-forming units per gram of nanofibrillar cellulose hydrogel is determined by preparing a dilution series of the hydrogel and by plating the dilution series on separate Petrifilm plates (3M) for aerobic bacteria (aerobic plate count) and for yeasts and moulds. The plates for aerobic bacteria are allowed to grow at 37° C. for 2 days and the plates for yeasts and moulds at 30° C. for 3-5 days, after which the colonies are counted. The number of colony-forming units of aerobic heterotrophs are determined by culturing the sample on plate count agar at a temperature of 37° C. for three (3) days. Alternatively, the presence of yeasts and/or fungi can be determined by culturing on potato dextrose agar at a temperature of 25° C. for five (5) days. Before the measurement, the samples are diluted ten-fold. The presence of anaerobic micro-organisms can be determined by culturing on brewer anaerobic agar for anaerobic bacterial count at a temperature of 30° C. for three (3) days in anaerobic conditions. Before the measurement, the samples are diluted ten-fold.

In an embodiment, the number of colony-forming units is determined by following the standard ISO 8784-1 (Pulp, Paper and board—Microbiological examination. Part 1: Total count of bacteria, yeast and mould based on disintegration). The results are given as the number of colony-forming units per gram of the sample.

In an embodiment, the number of colony-forming units of viable micro-organism per gram of nanofibrillar cellulose hydrogel may be measured by incubating at 37° C. for 14 days following the USP XXIV Chapter 71 sterility test.

Sterile nanofibrillar cellulose hydrogel may comprise fewer than 1 CFU, or fewer than $10^{-1}$ CFU, or fewer than $10^{-2}$ CFU, or fewer than $10^{-3}$ CFU, or fewer than $10^{-4}$ CFU, or fewer than $10^{-3}$ CFU, or fewer than $10^-$ CFU of a viable micro-organism per unit of the nanofibrillar cellulose hydrogel. The term "a viable micro-organism" may refer to one or more viable micro-organisms of the same or different species or strains. In other words, if the nanofibrillar cellulose hydrogel comprises fewer than $10^{-6}$ CFU of a viable micro-organism per unit of the nanofibrillar cellulose hydrogel, there is a probability of not more than one viable micro-organism in one million units of the nanofibrillar cellulose hydrogel; or less than one produced unit of the nanofibrillar cellulose hydrogel in a million is exposed to the risk of not being absolutely free of viable micro-organisms. The unit may be one gram of the nanofibrillar cellulose hydrogel. The unit may also be a package containing 1 g, 5 g or 10 g of nanofibrillar cellulose hydrogel. The unit may further be a multiwell plate containing nanofibrillar cellulose hydrogel in one or more wells or a single well of a multiwell plate containing nanofibrillar cellulose hydrogel.

Sterile nanofibrillar cellulose hydrogel may thus comprise fewer than 1 CFU, or fewer than $10^{-1}$ CFU, or fewer than $10^{-2}$ CFU, or fewer than $10^{-3}$ CFU, or fewer than $10^{-4}$ CFU, or fewer than $10^{-3}$ CFU, or fewer than $10^{-6}$ CFU of a viable micro-organism per gram of the nanofibrillar cellulose hydrogel. In other words, if the nanofibrillar cellulose hydrogel comprises fewer than $10^{-6}$ CFU of a viable micro-organism per gram of the nanofibrillar cellulose hydrogel, there is a probability of less than one viable micro-organism in one million grams of the nanofibrillar cellulose hydrogel.

The degree of sterility of the nanofibrillar cellulose hydrogel that is required may depend e.g. on its intended use.

In the context of this specification, the term "sterilization" or "sterilization process" may refer to any physical or chemical process capable of destroying all life forms and micro-organisms in particular and of inactivating viruses. A sterilization treatment or process may destroy life forms to a varying extent depending on the conditions and the micro-organism. For instance, autoclaving at a temperature of about 121° C. and at high pressure for a time period of about 15-20 minutes is typically an overkill sterilization process and capable of reducing the number of viable micro-organisms by a factor of at least $10^{12}$. It may therefore be considered an overkill autoclaving process.

It may not be necessary that the cellulose fibers are bleached, i.e. any cellulose fibers may, in principle, be used instead of bleached cellulose fibers. However, bleaching of cellulose fibers, e.g. at a chemical pulp mill, where the bleaching may be an oxidizing process comprising both acidic and alkaline stages, is capable of reducing the number of viable microorganisms present in the cellulose. When cellulose pulp fibers are obtained after bleaching, the number of viable microorganisms present in the cellulose pulp fibers is typically small or very small. The conditions of obtaining the bleached cellulose pulp fibers may be such that viable micro-organisms are not introduced into the cellulose pulp fibers, the aqueous suspension thereof and/or nanofibrillar cellulose hydrogel during the process.

In the context of this specification, the term "bleached cellulose pulp fibers" may refer to cellulose pulp fibers obtainable from a chemical pulping process, wherein it has been subjected to at least one bleaching stage or treatment.

It may, in principle, refer to bleached cellulose pulp fibers obtainable from any stage during bleaching stages. The bleached cellulose pulp fibers may also be obtainable from any stage immediately following the bleaching stage(s).

Bleaching stages may be alkaline or acidic. Commonly the bleaching stages may comprise an acidic A stage followed by a D stage without a washing stage between them (the so called A/D1 bleaching stage).

The bleached cellulose pulp fibers may be obtainable from an A, D, D1, A/D or A/D1 bleaching stage. "A" should be understood as referring to an acidic bleaching stage. "D" should be understood as referring to a chlorine dioxide bleaching stage. A, D and D1 stages may be stages separate from each other; each of A, D and D1 stages should however in this context be understood as being bleaching stages.

For instance, the bleached cellulose pulp fibers may be obtainable from the last washing stage after acidic and chlorine dioxide bleaching stages.

The bleached cellulose pulp fibers may be obtained e.g. via a sampling apparatus such as a tap or valve, through which bleached cellulose pulp fibers from a pulp mill fiberline may pass to a container and/or to a pipeline. Such a sampling apparatus, container and/or pipeline may be treated to minimize the presence of viable microorganisms e.g. by sterilizing. As a fiberline of a pulp mill may not operate under aseptic conditions, the bleached cellulose pulp fibers may be obtained from a pulp mill fiberline so as to minimize contamination by micro-organisms, e.g. via a sampling apparatus to a container that is disinfected or sterilized and by closing the container immediately when the bleached cellulose pulp fibers have been collected therein.

If a liquid, such as water or an aqueous solution, is added to provide the aqueous suspension, the liquid may be sterile, e.g. sterile water or a sterile aqueous solution. The water may also be distilled or deionized. Sterile distilled or deionized water does not introduce significant amounts of viable micro-organisms into the suspension and may make disintegrating the cellulose pulp fibers into nanofibrillar cellulose easier as compared to e.g. sterile tap water.

In the context of this specification, conditions of ISO 8 of ISO 14644-1 cleanroom standards or stricter may refer to conditions assigned to and reproducibly meeting a cleanroom classification (ISO 14644-1 cleanroom standards) of at least Class ISO 8, or at least ISO 7, or at least ISO 6, or at least ISO 5, or at least ISO 4, or at least ISO 3, or at least ISO 2, or ISO 1. The conditions stricter than conditions of ISO 8 of ISO 14644-1 cleanroom standards may thus refer to conditions of at least ISO 7 of ISO 14644-1 cleanroom standards, such as conditions of ISO 7, ISO 6, ISO 5, ISO 4, ISO 3, ISO 2 or ISO 1. Such conditions are aimed at minimizing or preventing the introduction or contamination of viable microorganisms into the process, in contact with the bleached cellulose pulp fibers or the suspension containing said bleached cellulose pulp fibers and in contact with the nanofibrillar cellulose hydrogel.

In the context of this specification, the conditions of ISO 8 of ISO 14644-1 cleanroom standards or stricter may include performing all steps of the process after providing the bleached cellulose pulp fibers in an environment that has a controlled level of contamination by micro-organisms and particles, such as a cleanroom or a building, or a segregated segment of it, containing a processing room in which air supply, materials, and equipment are regulated to control microbial and particle contamination. Conditions of ISO 14644-1 cleanroom standard ISO 5 or stricter may also be used, or ISO 4, or ISO 3, or ISO 2, or ISO 1.

The environment that has a controlled level of contamination by micro-organisms and particles is designed or adapted, maintained, and controlled to prevent particle and microbiological contamination of the cellulose pulp fibers and/or nanofibrillar cellulose hydrogel being processed.

Ventilation air to the environment may be e.g. filtered. The requirements for the environment may depend on other conditions of the process—for instance, if the process is not fully closed, higher requirements for microbial and particle contamination may be used for the environment.

The process may also comprise using aseptic techniques of working and of handling the cellulose pulp fibers and/or nanofibrillar cellulose hydrogel and any material that is to be in contact with the cellulose pulp fibers and/or nanofibrillar cellulose hydrogel.

After providing the aqueous suspension of the bleached cellulose pulp fibers, the following process steps may be performed in a closed environment so that the cellulose pulp fibers and/or the nanofibrillar cellulose hydrogel are transported from one process step to the next using aseptic connections, such as pipelines.

The process may also comprise using components, such as containers, reactors, pumps and connections, of a system for producing the nanofibrillar cellulose hydrogel that are configured to be in contact with the cellulose pulp fibers and/or nanofibrillar cellulose that are decontaminated, e.g. sterilized. Said components may provide uncompromised, continuous isolation of their interior from the external environment.

The process may also comprise using liquids, reagents or additives, such as water used for washing or diluting the cellulose pulp fibers and/or the nanofibrillar cellulose hydrogel, that are in contact with or added to the cellulose pulp fibers and/or the nanofibrillar cellulose hydrogel, that are sterilized, i.e. sterile. Said reagents or additives may be sterile or essentially sterile. For instance, autoclaved or sterile filtered water may be used.

Said all steps of the process after providing the bleached cellulose pulp fibers include subjecting the cellulose pulp fibers in the aqueous suspension to at least 2 cycles of high pressure mechanical disintegration to obtain a nanofibrillar cellulose hydrogel and thereby reducing the number of viable microorganisms present in the suspension by a factor of at least $10^2$. They may also include any subsequent optional processing steps, such as washing, any further decontamination treatment and packaging.

The process may further comprise washing the cellulose pulp fibers with a sterile liquid prior to subjecting to the high pressure mechanical disintegration. The sterile liquid may be e.g. sterile water or a sterile aqueous solution. The water may also be distilled or deionized. Sterile distilled or deionized water does not introduce significant amounts of viable micro-organisms into the suspension and may make disintegrating the cellulose pulp fibers into nanofibrillar cellulose easier as compared to e.g. sterile tap water. The washing may also be capable of reducing the number of viable microorganisms present in the suspension of the bleached cellulose pulp fibers. The washing may be performed e.g. by thickening the suspension of the cellulose pulp fibers in a filter press and redispersing the cellulose pulp fibers in the sterile liquid.

The process may also comprise adjusting the concentration (i.e. consistency) of the cellulose pulp fibers in the suspension prior to the high pressure mechanical disintegration. Adjusting the concentration of the cellulose pulp fibers may be done e.g. when the consistency of the disintegrated nanofibrillar cellulose hydrogel obtained would otherwise be too thick for feeding or pumping. The concentration may be adjusted e.g. to a concentration that is equal to or less than 3% (w/w) or 2% (w/w). If adjusting by adding a liquid in the nanofibrillar cellulose hydrogel, the liquid may be a sterile liquid.

The process may further comprise prerefining the cellulose pulp fibers to break down the cellulose pulp fibers prior to subjecting to the high pressure mechanical disintegration. The prerefining may be conducted using a mechanical prerefining apparatus, e.g. a PFI mill, a refiner, such as a Voith refiner using fibrillating blades, or a grinder mill. The prerefining has the technical effect of mechanically breaking down the cellulose pulp fibers. The cellulose pulp fibers are not completely fibrillated during the prerefining, but the structure of the cellulose pulp fibers is broken to some extent (i.e. partially), and it may thereby prevent blockage of a disintegrating apparatus used for high pressure mechanical disintegration of the cellulose pulp fibers. The prerefining may also reduce the number of viable microorganisms to some extent. The prerefining may also be performed under conditions of ISO 8 of ISO 14644-1 cleanroom standards or stricter. The means or equipment for prerefining cellulose pulp fibers may also be decontaminated or sterilized, i.e. essentially sterile.

The process may further comprise subjecting the bleached cellulose pulp fibers to an ion exchange treatment prior to prerefining and/or subjecting to the high pressure mechanical disintegration.

The solid matter content of the aqueous suspension of bleached cellulose pulp fibers for ion exchange may range from 0.1 to 20% by weight, suitably from 0.5 to 3% by weight. The ion exchange may be effected by subjecting the aqueous suspension of cellulose pulp fibers to a mild acid treatment for removing positively charged ions, followed by a treatment with a base containing defined, positively charged ions, for replacing the earlier ions. The suspension of cellulose pulp fibers that has been subjected to ion exchange may subsequently be prerefined and subjected to high pressure mechanically disintegration. The ion exchange of at least part of the carboxyl groups present in the cellulose pulp, e.g. with Na+, may comprise adjusting the pH of the aqueous suspension of cellulose pulp fibers to a value below 5.0, or below 4.0, using an inorganic or organic acid; removing of water to yield solid matter, washing the solid matter with water, and forming an aqueous suspension of the solid matter; adding at least one water soluble salt of $NH_4^+$, alkali metal or alkaline earth metal or metal to the formed suspension; adjusting the pH of the suspension to a value above 7.0 using an inorganic base; removing of water to yield solid matter, washing the solid matter with water, preferably distilled or deionized water, to yield ion-exchanged cellulose pulp; and forming an aqueous suspension of the ion exchanged cellulose pulp fibers.

In the ion exchange treatment, the water soluble salt of $NH_4^+$, alkali metal, alkaline earth metal or metal may be used in an amount to obtain a concentration of 0.001 to 0.01M (0.1 to 1 mol/kg fiber or solid material), particularly of 0.002 to 0.008M. In the ion exchange treatment, the content of solid matter in the suspension may range from 0.1 to 20% by weight, or from 0.5 to 3% by weight. The inorganic or organic acid may be an acid which can be easily washed away, leaves no undesirable residues in the product and has a pKa value between −7 and 7. The organic acid may be selected from short chain carboxylic acids, such as acetic acid, formic acid, butyric acid, propionic acid, oxalic acid and lactic acid. The term "short chain carboxylic acid" may refer to C1-C8 acids. The inorganic acid may be selected from hydrochloric acid, nitric acid, hydrobromic acid and sulphuric acid. The acid may be used as a dilute, from 0.001 to 5M aqueous solution, which can be conveniently added to the suspension. The addition time of the acid may be between 0.2 to 24 hours. The pH may be adjusted using the acid to a value below 5.0, or below 4.0, or below 3.0. Water used in the ion exchange treatment may be sterile tap water, sterile distilled water, sterile deionized water, or sterile purified water. The solid matter may be washed 1-5 times, or 2-3 times, with water after acid treatment to remove excess acid. The water soluble salt of $NH_4^+$, alkali metal, alkaline earth metal or metal may be selected from inorganic salts, complexes and salts formed with organic acids, of $NH_4^+$, alkali metal, alkaline earth metal or metals, such as $NH_4^+$, Na, K, Li, Ag and Cu. The inorganic salt may be sulphate, nitrate, carbonate or bicarbonate salt, such as $NaHCO_3$, $KNO_3$ or $AgNO_3$. The inorganic base may selected from NaOH, KOH, LiOH and $NH_3$. The pH of the suspension may be adjusted with the inorganic base to more than 7, such as from 7.5 to 12, or from 8 to 9. After the pH adjustment with the inorganic base, the water removal may be carried out and the solid matter may be washed with distilled or deionized water, for instance until the conductivity of the used washing liquid, such as filtrate, is less than 200 µS/cm, or less than 100 µS/cm, or less than 20 µS/cm.

Disintegrating the cellulose pulp fibers to obtain a nanofibrillar cellulose hydrogel results in the fibrillation of the cellulose pulp fibers.

The term "fibrillating" or "fibrillation" may be used interchangeably with expression "disintegrating" or "disintegration", and generally refers to disintegrating the cellulose pulp fibers mechanically by work applied to the fibers, where cellulose fibrils are liberated from the fibers or fiber fragments. The work may, in principle, be based on various effects, like grinding, crushing or shearing, or a combination of these, or another corresponding action that delaminates the cell walls of the fibers and liberates fibrils. However, in the context of the present method, high pressure mechanical disintegration that utilizes high shearing forces to a great extent may be preferred. The disintegrating may be performed at conditions wherein water is sufficiently present to prevent the formation of bonds between the fibers. The NFC hydrogel may be manufactured in a consistency of from 0.05 to 6% w/w, such as from 0.1 to 4% w/w, such as from 0.12 to 1.2% w/w, said consistencies being convenient for the fibrillation and the handling of the NFC hydrogel.

The means or equipment for high pressure mechanical disintegration of the cellulose pulp fibers may also be decontaminated or sterilized, i.e. essentially sterile.

The present inventors have found that subjecting the cellulose pulp fibers in the aqueous suspension to high pressure mechanical disintegration may reduce the number of viable microorganisms present in the suspension significantly. The high pressure mechanical disintegration thus may have an antimicrobial effect. The high pressure mechanical disintegration may be capable of reducing the number of viable micro-organisms present in an aqueous suspension of cellulose pulp fibers to be fibrillated by e.g. at least a factor of $10^2$.

In the context of this specification, the term "high pressure mechanical disintegration" may be understood as referring to disintegration of optionally pre-refined cellulose pulp fibers using a high pressure.

The high pressure mechanical disintegration may be conducted using a pressure type homogenizer to obtain a nanofibrillar cellulose hydrogel, thereby reducing the number of viable microorganisms present in the suspension. The pressure type homogenizer may be e.g. a high pressure homogenizer or a high pressure fluidizer, such as a microfluidizer, macrofluidizer or a fluidizer-type homogenizer.

A high pressure homogenizer or a high pressure fluidizer may comprise one or more flow restrictions, such as one or more valves or flow chambers, through which the suspension is forced so that pressure in the suspension is increased at the flow restriction. This may create conditions of high turbulence and shear, combined with compression, acceleration, pressure drop and impact, and may cause disintegration of particles throughout the suspension. Such equipment may also be particularly efficient in reducing the number of viable microorganisms present in the suspension.

The process may comprise subjecting the cellulose pulp fibers in the aqueous suspension to at least 6 cycles (also referred to as passes or rounds). The process may also comprise subjecting the cellulose pulp fibers in the aqueous suspension to 2 to 10 cycles, or 6 to 7 cycles of high pressure mechanical disintegration. When at most 10 cycles are used, the resulting nanofibrillar cellulose hydrogel may have a zero shear viscosity of at least 100 Pa·s, as measured in a consistency of 0.5% (w/w) in water. Such a zero shear viscosity may be desirable. The process may, for example, comprise subjecting the cellulose pulp fibers to 2, 3, 4, 5, 6, 7, 8, 9, or 10 cycles of high pressure mechanical disintegration.

The pressure may range between 300-2000 bar. The pressure may also be at least 600 bar, or at least 1500 bar. The pressure may be, for example, 300, 400, 500, 600, 700, 800, 900, 1000, 1100, 1200, 1300, 1400, 1500, 1600, 1700, 1800, 1900, or 2000 bar.

As an example, a high pressure homogenizer may operate at a pressure of 400 to 600 bar for at most 10 cycles. As a further example, a high pressure fluidizer may operate at a pressure of 1500 bar for at most 10 cycles.

The consistency (concentration) of the aqueous suspension subjected to the high pressure mechanical disintegration may be at least 0.7% (w/w), or 0.7 to 3% (w/w). At lower or higher consistencies the disintegration and/or the ability of the disintegration to reduce the number of viable microorganisms may suffer.

The process may comprise subjecting the cellulose pulp fibers in the aqueous suspension to at least 2 cycles of high pressure mechanical disintegration to obtain a nanofibrillar cellulose hydrogel and thereby reducing the number of viable microorganisms present in the suspension by a factor of at least $10^3$. The number of cycles of the high pressure mechanical disintegration and other possible variables may be selected so as to achieve a desired reduction in the number of viable microorganisms present in the suspension.

A nanofibrillar cellulose hydrogel obtainable by the process may already be essentially sterile after the high pressure mechanical disintegration. However, it is also possible to further reduce the number of viable micro-organisms in the nanofibrillar cellulose hydrogel after the high pressure mechanical disintegration.

Therefore the process may comprise subjecting the nanofibrillar cellulose hydrogel to a further decontamination treatment for reducing the number of viable micro-organisms in the nanofibrillar cellulose hydrogel. The further decontamination treatment may be capable of reducing the number of viable micro-organisms by a factor of at least $10^2$, or at least $10^3$, or at least $10^4$, or at least $10^6$, or at least $10^8$, or at least $10^{10}$, or by a factor in the range of $10^2$ to $10^{10}$, or by a factor in the range of $10^2$ to $10^8$.

In the context of this specification, the term "decontamination treatment" may refer to any physical or chemical treatment capable of reducing the number of viable life forms and micro-organisms in particular and of inactivating viruses. Various suitable further decontamination treatments may, in principle, be used. Overkill autoclaving is not, however, considered to be a decontamination treatment in this context.

The further decontamination treatment may comprise subjecting the nanofibrillar cellulose hydrogel to non-ionizing or ionizing radiation. The non-ionizing radiation may be e.g. ultraviolet light irradiation, e.g. by ultraviolet light in the ultraviolet C range (having a wavelength in the range of approx. 280-100 nm) or by ultraviolet light having a wavelength in the range of 200 to 300 nm, for instance about 250 nm. The dose of the ultraviolet light irradiation may vary, e.g. in the range of 5-5000 mJ/cm$^2$, depending on factors such as the flow regime (e.g. thin film, laminar, turbulent, coiled-tube etc.) or the turbidity of the nanofibrillar cellulose hydrogel. Further, the thickness of the layer of the nanofibrillar cellulose hydrogel that is irradiated has an effect on the effectiveness of the ultraviolet light irradiation. The ionizing radiation may be e.g. irradiation with gamma rays, X-rays, or subatomic particles such as electrons. Small doses, such as doses in the range of about 1-50 kGy, or about 2-25 kGy, may be sufficient. Ionizing radiation may be capable of disrupting the structures of cells of viable microorganisms.

The further decontamination treatment may comprise subjecting the nanofibrillar cellulose hydrogel to a heat treatment, wherein the heat treatment comprises keeping the nanofibrillar cellulose hydrogel at a temperature in the range of 72° C. to 100° C. for at least 15 seconds. If the hydrogel is not allowed to boil, deterioration of the hydrogel caused by the high temperature may be avoided, and the need to use pressurized equipment may also be avoided, thereby making the process more safe and simple.

For example, the heat treatment may comprise keeping the nanofibrillar cellulose hydrogel at a temperature of 89° C. for 1.0 s; at 90° C. for 0.5 s; at 94° C. for 0.1 s; or at 96° C. for 0.05 s.

Such a heat treatment of the nanofibrillar cellulose hydrogel may have the effect of reducing or eliminating the number of viable micro-organisms in the hydrogel without compromising, in an adverse extent, other properties, such as the viscosity, of the nanofibrillar cellulose hydrogel, which would affect its suitability to be further used in e.g. cosmetic or pharmaceutical products or devices. The heat treatment may not affect the viscosity of the hydrogel in a similar manner as e.g. overkill autoclaving does.

The temperature and the duration of the heat treatment may be selected so that the number of viable microorganisms present in the suspension is reduced by a factor of up to 10$^6$. The temperature and the duration of the heat treatment may also be selected so that the number of viable microorganisms present in the suspension is reduced by a factor of at least 10$^2$.

The operating pressures are to be selected so that the nanofibrillar cellulose hydrogel is not boiling in the used temperature. The pressure in the nanofibrillar cellulose hydrogel in the treatment temperature may be higher than vapour pressure of water.

The nanofibrillar cellulose hydrogel to be subjected to heat treatment may have a dry matter content of at least 0.6 weight-%, or at least 0.7 weight-%, or at least 0.8 weight-%, or at least 0.9 weight-%, or at least 1 weight-%. The nanofibrillar cellulose hydrogel to be subjected to heat treatment may also have a dry matter content of at most 4 weight-%, or at most 3 weight-%, or at most 2 weight-%. The nanofibrillar cellulose hydrogel to be subjected to heat treatment may also have a dry-matter content of 0.6-4 weight-%, or 0.7-3 weight-%, or 0.8-3 weight-%, or 0.9-2 weight-%. Such hydrogels may be more resistant to possible adverse effects of the heat treatment to the properties of the hydrogel.

The further decontamination treatment may also comprise subjecting the nanofibrillar cellulose hydrogel to pulsed electric field processing. Pulsed electric field processing may be performed at a temperature of up to 50° C. The nanofibrillar cellulose hydrogel may be placed between two electrodes and exposed to an electrical field in the form of very short, high-voltage pulses. Electric field strengths of e.g. in the range of 20 to 50 kV/cm, pulse lengths e.g. in the range of 1 to 10 µs and specific energy inputs of e.g. in the range of 50 to 1000 kJ/kg may be used; however, the parameters may be adjusted so as to allow a suitable reduction in the number of viable microorganisms.

The further decontamination treatment may not comprise autoclaving or overkill autoclaving the nanofibrillar cellulose hydrogel. The term "autoclaving" or "overkill autoclaving" may, in the context of this specification, be understood as referring to a process of subjecting nanofibrillar cellulose hydrogel to saturated steam at a temperature of about 121° C., or at a temperature of at least 120° C., for a time period of at least 10 minutes, or at least 15 minutes. Autoclaving is typically done at a pressure of at least 15 µsi in excess of atmospheric pressure.

The process may comprise thereby obtaining a nanofibrillar cellulose hydrogel that contains fewer than 10$^{-1}$, or fewer than 10$^{-2}$, or fewer than 10$^{-3}$, or fewer than 10$^{-4}$, or fewer than 10$^{-5}$, or fewer than 10$^{-6}$ CFU of a viable micro-organism for a unit of 1 gram of the nanofibrillar cellulose hydrogel.

The process may comprise thereby obtaining a non-autoclaved nanofibrillar cellulose hydrogel that contains fewer than 10$^{-1}$, or fewer than 10$^{-2}$, or fewer than 10$^{-3}$, or fewer than 10$^{-4}$, or fewer than 10$^{-5}$, or fewer than 10$^{-6}$ CFU of a viable micro-organism for a unit of 1 gram of the nanofibrillar cellulose hydrogel.

The turbidity value of the nanofibrillar cellulose hydrogel after the further decontamination treatment, such as heat treatment, may be at most 5%, or at most 10%, higher than the turbidity value of the nanofibrillar cellulose hydrogel before the further decontamination treatment, as measured at a 0.1% (w/w) concentration of the nanofibrillar cellulose in water.

The pH of the nanofibrillar cellulose hydrogel after the further decontamination treatment, such as heat treatment, may be at most 0.4, or at most 0.2, pH units lower than the pH of the nanofibrillar cellulose hydrogel before the further decontamination treatment. As pH units are expressed on a logarithmic scale, a difference of e.g. 0.2 pH units may be considered significant for certain purposes. The pH may be measured at a temperature of 20° C.

The nanofibrillar cellulose hydrogel after the process may have a viscosity of at least 2000 mPa·s, or at least 7000 mPa·s, or 2000-50 000 mPa·s, or 7000-40 000 mPa·s, as measured at a 0.8% (w/w) concentration of the nanofibrillar cellulose in water with a Brookfield viscometer at a temperature of 20° C., with a vane spindle and a measuring speed of 10 rpm.

Native nanofibrillar cellulose hydrogel after the process may have a viscosity of at least 2000 mPa·s, or at least 7000 mPa·s, or 2000-16 000 mPa·s, or 7000-13 000 mPa·s, as measured at a 0.8% (w/w) concentration of the nanofibrillar cellulose in water with a Brookfield viscometer at a temperature of 20° C., with a vane spindle and a measuring speed of 10 rpm.

Native nanofibrillar cellulose hydrogel after the process may have a zero shear viscosity in the range of 100-8 000 Pa·s, or 200-2 000 Pa·s, or 300-1 000 Pa·s, when dispersed to a concentration of 0.5 w % in water. It may also have a yield stress in the range of 0.5-8 Pa, or 1-4 Pa, when dispersed to a concentration of 0.5 w % in water.

Anionic nanofibrillar cellulose after the process may have a zero shear viscosity in the range of 1000-100 000 Pa·s, or 5000-50 000 Pa·s, when dispersed to a concentration of 0.5 w % in water. It may also have a yield stress in the range of 1-50 Pa, or 3-20 Pa, when dispersed to a concentration of 0.5 w % in water.

After subjecting the suspension to the high pressure mechanical disintegration, the nanofibrillar cellulose hydrogel may be diluted to a consistency suitable for packaging using any sterile liquid suitable for the end use of the nanofibrillar cellulose hydrogel, such as sterile water, a sterile growth medium for cell culture, or a sterile buffer solution.

The process may further comprise packaging the nanofibrillar cellulose hydrogel into units. The packaging may also be done under conditions of ISO 5 of ISO 14644-1 cleanroom standards or stricter. The nanofibrillar cellulose hydrogel may be packaged into units of e.g. 1 g, 5 g, 10 g or 100 g, for instance in ampules or other suitable containers. The nanofibrillar cellulose hydrogel may also be packaged into multiwell plates. The units may be packaged in containers that are decontaminated or sterilized, i.e. essentially sterile.

The process may further comprise packaging the nanofibrillar cellulose hydrogel into units aseptically.

The process may comprise maintaining conditions of ISO 5 of ISO 14644-1 cleanroom standards or stricter from the high pressure mechanical disintegration to packaging the nanofibrillar cellulose hydrogel.

The number of viable microorganisms may be reduced during the process by a factor of at least $10^3$, or at least $10^4$, or at least $10^6$, or at least $10^{12}$. This factor may be calculated on the basis of the number of viable micro-organisms originally present in the suspension of the cellulose pulp fibers, and on the basis of the number of viable micro-organisms present in the nanofibrillar cellulose hydrogel obtainable by the process.

The nanofibrillar cellulose may, in principle, be any nanofibrillar cellulose. It may also be native nanofibrillar cellulose or anionic nanofibrillar cellulose.

Anionic nanofibrillar cellulose can be formed by a pretreatment capable of oxidizing at least part of the hydroxyl groups of cellulose into carboxyl groups. For instance, about 10-15% of the hydroxyl groups of cellulose may be oxidized into carboxyl groups. The anionic nanofibrillar cellulose may be formed by oxidizing cellulose pulp fibers e.g. using known TEMPO oxidizing processes.

Native nanofibrillar cellulose may be obtainable from washed, ion exchanged or enzymatically pretreated pulp. Typically, native nanofibrillar cellulose has wider fibril diameter while the chemically modified, anionic nanofibrillar cellulose is much thinner and has a continuous network. The number average fibril diameter of the cellulose nanofibril may be suitably from 1-200 nm. The number average fibril diameter of native grades may be 1-100 nm, and in chemically modified, anionic grades 1-20 nm. Size distribution is typically also narrower for the modified grades.

The process may thus be a process for producing a sterile or essentially sterile native nanofibrillar cellulose hydrogel.

The process may be carried out in a continuous mode.

The process according to one or more embodiments may allow for producing a nanofibrillar cellulose hydrogel that is essentially sterile but the properties of which, such as high viscosity and turbidity, do not suffer, as opposed e.g. to nanofibrillar cellulose hydrogel that has been overkill autoclaved.

A nanofibrillar cellulose hydrogel is disclosed, wherein the nanofibrillar cellulose hydrogel is sterile and non-autoclaved. Non-autoclaved may refer to nanofibrillar cellulose hydrogel that is not overkill autoclaved.

A nanofibrillar cellulose hydrogel obtainable by the process according one or more embodiments is also disclosed.

The nanofibrillar cellulose hydrogel obtainable by the process according to one or more embodiments may be sterile or essentially sterile.

The nanofibrillar cellulose hydrogel may have a viscosity of at least 2000 mPa·s, or at least 7000 mPa·s, or 2000-50 000 mPa·s, or 7000-40 000 mPa·s, as measured at a 0.8% (w/w) concentration of the nanofibrillar cellulose in water with a Brookfield viscometer at a temperature of 20° C., with a vane spindle and a measuring speed of 10 rpm.

Native nanofibrillar cellulose hydrogel may have a viscosity of at least 2000 mPa·s, or at least 7000 mPa·s, or 2000-16 000 mPa·s, or 7000-13 000 mPa·s, as measured at a 0.8% (w/w) concentration of the nanofibrillar cellulose in water with a Brookfield viscometer at a temperature of 20° C., with a vane spindle and a measuring speed of 10 rpm.

The so-called Brookfield viscosity measurement can be performed in the following manner: A vane spindle (number 73) is selected and the Brookfield-viscosity measuring apparatus (Brookfield RVDV-III) is started. A sample of the nanofibrillar cellulose is diluted to a concentration of 0.8% by weight in water and mixed for 10 minutes using a propel mixer at 700-800 rpm. No ultrasound mixing is used. The diluted sample mass is added to a 250 ml beaker and the temperature is adjusted to 20° C.±1° C., heated if necessary and mixed. The spindle is inserted in the beaker and measuring is started. 300 points are registered starting with 0.5 rpm speed, then 300 points with 5 rpm and 10 rpm, and 100 points with 50 rpm and 100 rpm speeds. Relative viscosity is measured from each sample mass twice. Mean value and standard deviation are calculated for each sample, from results obtained from parallel measurements during the last 5 seconds.

Native nanofibrillar cellulose hydrogel may have a zero shear viscosity in the range of 100-8 000 Pa·s, or 200-2 000 Pa·s, or 300-1 000 Pa·s, when dispersed to a concentration of 0.5 w % in water. It may also have a yield stress in the range of 0.5-8 Pa, or 1-4 Pa, when dispersed to a concentration of 0.5 w % in water.

Anionic nanofibrillar cellulose hydrogel may have a zero shear viscosity in the range of 1000-100 000 Pa·s, or 5000-50 000 Pa·s, when dispersed to a concentration of 0.5 w % in water. It may also have a yield stress in the range of 1-50 Pa, or 3-20 Pa, when dispersed to a concentration of 0.5 w % in water.

The nanofibrillar cellulose hydrogel may comprise fewer than $10^{-6}$ CFU of a viable microorganism for a unit of 1 gram of the nanofibrillar cellulose hydrogel.

The sterile nanofibrillar cellulose hydrogel may comprise fewer than $10^{-1}$, or fewer than $10^{-2}$, or fewer than $10^{-3}$, or fewer than $10^{-4}$, or fewer than $10^{-3}$, or fewer than $10^{-6}$ CFU of a viable micro-organism per unit of the nanofibrillar cellulose hydrogel. A unit may be e.g. 1 g, 5 g, 10 g or 100 g of the nanofibrillar cellulose hydrogel, for instance in an ampule. The unit may also be a multiwell plate containing the nanofibrillar cellulose hydrogel in one or more wells, or a single well of a multiwell plate.

The sterile nanofibrillar cellulose hydrogel may comprise fewer than $10^{-1}$, or fewer than $10^{-2}$, or fewer than $10^{-3}$, or fewer than $10^{-4}$, or fewer than $10^{-3}$, or fewer than $10^{-6}$ CFU of a viable micro-organism per gram of the nanofibrillar cellulose hydrogel.

The sterile nanofibrillar cellulose hydrogel may comprise fewer than $10^{-1}$, or fewer than $10^{-2}$, or fewer than $10^{-3}$, or fewer than $10^{-4}$, or fewer than $10^{-3}$, or fewer than $10^{-6}$ CFU of a viable micro-organism for a unit of 1 gram of the nanofibrillar cellulose hydrogel.

The nanofibrillar cellulose hydrogel may have a turbidity value of at most 200 NTU at most 90 NTU, or at most 60 NTU, or at most 40 NTU, or 1 to 200 NTU, or 1 to 90 NTU, or 1 to 60 NTU, or 10 to 40 NTU, as measured at 0.1% (w/w) concentration of the nanofibrillar cellulose in water.

A turbidometric method based on nephelometry (90° angle between light source and detector) can be used for measuring the turbidity of samples. HACH P2100 Turbidometer, with a 50 ml measuring vessel may be used for turbidity measurements. The calibration of the apparatus is checked and controlled with standard calibration bottles/samples. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. Mean value and standard deviation are calculated for each sample.

The dry matter content can be determined e.g. according ISO 4119/1995, "Determination of stock concentration", with the exception that the sample is kept in an oven at a temperature of 105° C. overnight (t=16 h) and by weighing the sample before and after it is kept in the oven.

The nanofibrillar cellulose hydrogel may comprise e.g. 0.01-4% (w/w), or 0.1-2.5% (w/w), or 0.2-1.5% (w/w), or 0.2-1.2% (w/w), of nanofibrillar cellulose. The nanofibrillar cellulose hydrogel may also comprise 0.7-3% (w/w) of nanofibrillar cellulose.

The nanofibrillar cellulose hydrogel may be anionic nanofibrillar cellulose hydrogel. In other words, the nanofibrillar cellulose in the nanofibrillar cellulose hydrogel may be anionic nanofibrillar cellulose.

The nanofibrillar cellulose hydrogel may be native nanofibrillar cellulose hydrogel. In other words, the nanofibrillar cellulose in the hydrogel may be native nanofibrillar cellulose.

A nanofibrillar cellulose hydrogel according to one or more embodiments for use in therapy is disclosed.

Use of the nanofibrillar cellulose hydrogel according to one or more embodiments in a cosmetic product is also disclosed.

A growth medium for cell culture comprising the nanofibrillar cellulose hydrogel according to one or more embodiments is disclosed.

Use of the nanofibrillar cellulose hydrogel according to one or more embodiments in cell culture is disclosed.

A system for producing a nanofibrillar cellulose hydrogel comprises a high pressure mechanical disintegration apparatus for subjecting the cellulose pulp fibers in the aqueous suspension to at least 2 cycles of high pressure mechanical disintegration to obtain a nanofibrillar cellulose hydrogel and for reducing the number of viable microorganisms present in the suspension by a factor of at least $10^2$;

wherein the high pressure mechanical disintegration apparatus and any optional components of the system that are configured to or adapted to be in contact with the suspension and/or the nanofibrillar cellulose hydrogel are configured to or adapted to operate under conditions of ISO 8 of ISO 14644-1 cleanroom standards or stricter.

The system may also comprise means for obtaining bleached cellulose pulp fibers. The means for obtaining bleached cellulose pulp fibers may comprise e.g. a sampling apparatus such as a tap or valve, which may be configured to allow removal of bleached cellulose pulp fibers from a pulp mill fiberline, a container and/or a pipeline. Such means may be treated to minimize the presence of viable micro-organisms e.g. by sterilizing. As a fiberline of a pulp mill does not typically operate under aseptic conditions, the means for obtaining bleached cellulose pulp fiber may comprise e.g. a sampling apparatus configured to allow removal of bleached cellulose pulp fibers from a pulp mill fiberline and a container that is disinfected or sterilized and closable.

The high pressure mechanical disintegration apparatus may be a pressure type homogenizer, such as a high pressure homogenizer or a high pressure fluidizer, such as a microfluidizer, macrofluidizer or a fluidizer-type homogenizer.

The conditions stricter than ISO 8 of ISO 14644-1 cleanroom standards or stricter may correspond to ISO 14644-1 cleanroom standard ISO 7, or to ISO 6, or to ISO 5, or to ISO 4, or to ISO 3, or to ISO 2, or to ISO 1. The conditions may also be ISO 5 of ISO conditions of ISO 14644-1 cleanroom standards or stricter.

The system may further comprise a prerefining apparatus for prerefining the cellulose pulp fibers prior to the high pressure mechanical disintegration; wherein the prerefining apparatus is configured to or adapted to operate under conditions of ISO 8 of ISO 14644-1 cleanroom standards or stricter. The prerefining apparatus may be a mechanical prerefining apparatus, e.g. a PFI mill, a refiner, such as a Voith refiner using fibrillating blades, or a grinder mill.

The system may comprise a washing apparatus for washing the cellulose pulp fibers; wherein the washing apparatus is configured to operate under conditions of ISO 8 of ISO 14644-1 cleanroom standards or stricter. The washing apparatus may comprise e.g. a filter press for thickening the cellulose pulp fibers in the suspension and a pulper for redispersing the cellulose pulp fibers in water.

The system may comprise a decontamination apparatus for reducing the number of viable micro-organisms in the nanofibrillar cellulose hydrogel by a factor of at least $10^2$, or by a factor in the range of $10^2$ to $10^{10}$, or by a factor in the range of $10^2$ to $10^8$.

In the context of this specification, the term "decontamination apparatus" may refer to an apparatus configured to or adapted to perform any physical or chemical treatment capable of reducing the number of viable life forms and micro-organisms in particular and of inactivating viruses. The decontamination apparatus may however not be an apparatus configured to or adapted to autoclave or overkill autoclave the nanofibrillar cellulose hydrogel. The decontamination apparatus is also an apparatus different from the high pressure mechanical disintegration apparatus, even though the high pressure mechanical disintegration apparatus is also capable of decontaminating.

The decontamination apparatus may comprise e.g. a source of non-ionizing radiation, such as an ultraviolet lamp, or a source of ionizing radiation, such as a source of gamma rays, X-rays or of subatomic particles.

The decontamination apparatus may also comprise a heating apparatus. The heating apparatus may be configured to or adapted to heat and keep the nanofibrillar cellulose hydrogel at a temperature in the range of 72° C. to 100° C. for at least 15 seconds. The heating apparatus may be e.g. a heat exchanger. The temperature and the duration in which the heating apparatus is configured to or adapted to heat and keep the nanofibrillar cellulose may be selected so that the number of viable microorganisms present in the suspension is reduced by a factor of up to $10^6$, or by a factor of at least $10^2$, or by a factor in the range of $10^2$ to $10^{10}$ or $10^2$ to $10^8$.

The system may comprise a cooling apparatus for cooling the nanofibrillar cellulose hydrogel to a temperature of below 30° C. in at most 120 seconds. The cooling apparatus may be e.g. a heat exchanger. The system may also comprise a cooling apparatus, which is configured to cool the nanofibrillar cellulose hydrogel to a temperature of below 30° C.

The heating apparatus and the cooling apparatus may be the same apparatus or two different apparatuses.

The decontamination apparatus may also be an apparatus for pulsed electric field processing. The apparatus for pulsed electric field processing may be configured to or adapted to pulsed electric field processing of the nanofibrillar cellulose hydrogel.

The system may further comprise a packaging apparatus for packaging the nanofibrillar cellulose hydrogel. The packaging apparatus may be suitable for aseptic packaging e.g. in ampules.

Any or all components of the system that are configured to or adapted to be in contact with the cellulose pulp fibers and/or nanofibrillar cellulose may be decontaminated and configured to provide uncompromised, continuous isolation of their interior from the external environment when the system is in use. Any or all components of the system that are configured to or adapted to be in contact with the cellulose pulp fibers and/or nanofibrillar cellulose may also be sterilized. The any or all components of the system that are configured to be in contact with the cellulose pulp fibers and/or nanofibrillar cellulose may include e.g. the high pressure mechanical disintegration apparatus, the washing apparatus, the decontamination apparatus, the packaging apparatus, one or more pumps and connections between said apparatuses.

The system may be configured to exclude external contamination from the its interior by accomplishing material transfer via aseptic connection to auxiliary equipment, rather than via openings to the surrounding environment. Such a system may be configured to or adapted to remain sealed throughout the process when in use.

The system may also be configured to or adapted to allow for the continuous or semi-continuous ingress and/or egress of materials during the process, i.e. when in use, through one or more openings. The openings may be configured (e.g. using continuous overpressure) to or adapted to exclude the entry of external contamination into the system when in use.

The system may be a system for producing sterile nanofibrillar cellulose hydrogel.

The system may be a system for producing a native nanofibrillar cellulose hydrogel.

The system may be a system for producing a sterile native nanofibrillar cellulose hydrogel.

Use of a high pressure mechanical disintegration apparatus in the production of a nanofibrillar cellulose hydrogel from an aqueous suspension of cellulose pulp fibers for reducing the number of viable microorganisms present in the suspension is further disclosed.

The high pressure mechanical disintegration apparatus may be a pressure-type fluidizer, e.g. a high pressure homogenizer or a high pressure fluidizer, such as a microfluidizer, macrofluidizer or a fluidizer-type homogenizer.

The use of a high pressure mechanical disintegration apparatus in the production of a nanofibrillar cellulose hydrogel from an aqueous suspension of cellulose pulp fibers for reducing the number of viable microorganisms present in the suspension by a factor of at least $10^2$, or at least $10^3$, is disclosed.

The embodiments described hereinbefore may be used in any combination with each other. Several of the embodiments may be combined together to form a further embodiment. A process, a hydrogel, a system, or a use, to which the invention is related, may comprise at least one of the embodiments described hereinbefore.

Technical effects of one or more embodiments include that the number of viable microoganisms may be significantly reduced in nanofibrillar cellulose hydrogel without compromising the properties, such as viscosity, turbidity or pH, of the hydrogel, which would affect its suitability to be further used in e.g. cosmetic or pharmaceutical products or devices.

Technical effects of one or more embodiments include that a nanofibrillar cellulose hydrogel may be provided for use in pharmaceutical or cosmetic applications.

EXAMPLES

Reference will now be made in detail to the embodiments, an example of which is illustrated in the accompanying drawing.

FIG. 1 illustrates a system according to one embodiment for producing a nanofibrillar cellulose hydrogel. The system comprises means 1 for obtaining bleached cellulose pulp fibers. The means 1 may comprise e.g. a container or a pipeline that is sterilized.

The bleached cellulose pulp fibers may be provided to a washing apparatus 4 for washing the bleached cellulose pulp fibers. Sterilized water (or other sterilized liquid) may be provided to the washing apparatus 4 from a source of sterile water 6.

The sterilized water may be e.g. sterile filtered or autoclaved to ensure it is essentially sterile.

The system further comprises a prerefining apparatus 3 for prerefining the bleached cellulose pulp fibers. The prerefining apparatus 3 is configured to partially break down the bleached cellulose pulp fibers prior to high pressure mechanical disintegration.

The system also comprises a high pressure mechanical disintegration apparatus 2 for disintegrating the cellulose pulp fibers to obtain a nanofibrillar cellulose hydrogel. The high pressure mechanical disintegration apparatus 2, such as a fibrillation unit, is configured to fibrillate the cellulose pulp fibers. Suitable high pressure mechanical disintegration apparatuses may be e.g. a fluidizer, a homogenizer or other apparatuses that are configured to exert strong shear, turbulence, impact or pressure forces on the cellulose pulp fibers. The high pressure mechanical disintegration apparatus 2 may also be a high pressure homogenizer or a high pressure fluidizer. If desired, sterilized water may be provided from the source of sterile water 6 to the high pressure mechanical disintegration apparatus 2 to dilute the hydrogel obtainable in the high pressure mechanical disintegration apparatus 2. The nanofibrillar cellulose hydrogel obtained in the high pressure mechanical disintegration apparatus 2 may be provided to a decontamination apparatus 5 for a further decontamination treatment of the nanofibrillar cellulose hydrogel. The decontamination apparatus 5 may be e.g. a heating apparatus, wherein the hydrogel is subjected to a heat treatment. The heating apparatus may be configured to keep the nanofibrillar cellulose hydrogel at a temperature in the range of 72° C. to 100° C. for at least 15 seconds for reducing the number of viable micro-organisms in the nanofibrillar cellulose hydrogel. The decontamination apparatus 5 may alternatively comprise e.g. a source of non-ionizing radiation, such as an ultraviolet lamp, or a source of ionizing radiation, such as a source of gamma rays, X-rays or of subatomic particles.

The nanofibrillar cellulose hydrogel obtainable from the further decontamination treatment is packaged in a packaging apparatus 7 for packaging the nanofibrillar cellulose hydrogel. The packaging apparatus 7 is suitable for aseptic packaging e.g. into ampules, bottles, multiwell plates or other containers. They may be sterilized in a sterilization apparatus 8 for sterilizing containers for packaging the nanofibrillar cellulose hydrogel.

The system also comprises aseptic fluid connections configured to convey material, such the cellulose pulp fibers and the nanofibrillar cellulose hydrogel between parts of the system.

The washing apparatus 3, the high pressure mechanical disintegration apparatus 2, the decontamination apparatus 5 and the packaging apparatus 7 are configured to operate under conditions of ISO 8 of ISO 14644-1 cleanroom standards or even stricter. They may be decontaminated by further decontamination treatments prior to operation of the system. Fluid connections between components of the system that are configured to be in contact with or to convey material or fluid that is to be in contact with the cellulose pulp fibers and/or the nanofibrillar cellulose hydrogel are via aseptic connections.

The system further comprises a cleanroom 9 or another similar barrier for providing an environment that has a controlled level of contamination by micro-organisms and particles. The cleanroom operates under conditions of ISO 8 of ISO 14644-1 cleanroom standards or even stricter. Such a system may be configured to remain sealed throughout the process. The cleanroom 9 may be configured to exclude external contamination from the its interior by accomplishing material transfer via aseptic connection to auxiliary equipment, rather than via openings to the surrounding environment.

The cleanroom 9 may also be configured to allow for the continuous or semi-continuous ingress and/or egress of materials during the process through one or more openings. The openings may be configured (e.g. using continuous overpressure) to exclude the entry of external contamination into the system. Sterilized air, e.g. air filtered using a HEPA filter capable of removing particular matter and viable micro-organisms from the air, may be provided as vent air, if needed, to the cleanroom 9.

After the nanofibrillar cellulose hydrogel is packaged aseptically into suitable containers that preserve its sterility, the containers may be removed from the cleanroom 9.

Example 1—Preparing a Sterile Native Nanofibrillar Cellulose Hydrogel by Autoclaving A comparative example was provided by preparing a native nanofibrillar cellulose hydrogel by disintegrating cellulose pulp fibers into fibrils using an Atrex® homogenisator for 6, 8 or 10 rounds at a concentration of 2.5% (w/w) based on dry weight of the oxidized cellulose pulp fibers. The nanofibrillar cellulose hydrogel thus obtained was diluted to a concentration of 1.5% by mixing for 30 seconds using a Bamix® mixer. The diluted hydrogel was autoclaved at a temperature of 121° C. for 15 minutes. During the warmup before and the cooling after the autoclaving temperature, the temperature exceeded 80° C. for about 30 minutes.

The Brookfield viscosity of the hydrogel was measured before and after autoclaving.

Viscosity measurements of the nanofibrillar cellulose hydrogels were carried out as follows. A vane spindle (number 73) was selected and the Brookfield-viscosity measuring apparatus (Brookfield RVDV-III) was started. A sample of the nanofibrillar cellulose hydrogel was diluted to a concentration of 0.5% by weight in water and mixed for 10 min using a propel mixer 700-800 rpm. No ultrasound mixing was used for modified grades. The diluted sample mass was added to a 250 ml beaker and the temperature was adjusted to 20° C.±1° C., pH 7, heated if necessary and mixed. The spindle was inserted in the beaker and measuring was started. The program registered 300 points starting with 0.5 rpm speed, then 300 points with 5 rpm and 10 rpm, and 100 points with 50 rpm and 100 rpm speeds. Relative viscosity was measured from each sample mass twice. Mean value and standard deviation were calculated for each sample, from results obtained from parallel measurements during last 5 seconds.

For rheological measurement the following method was used. Measurement was carried out with a stress controlled rotational rheometer (ARG2, TA instruments, UK) equipped with four-bladed vane geometry. Samples were diluted with deionized water (200 g) to a concentration of 0.5 wt % and mixed with Waring Blender (LB20E*, 0.5 l) 3×10 sec (20 000 rpm) with short break between the mixing. Rheometer measurement was carried out for the sample, pH 7. The diameters of the cylindrical sample cup and the vane were 30 mm and 28 mm, respectively, and the length was 42 mm. The steady state viscosity of the hydrogels was measured using a gradually increasing shear stress of 0.001-1000 Pa. After loading the samples to the rheometer they were allowed to rest for 5 min before the measurement was started, room temperature. The steady state viscosity was measured with a gradually increasing shear stress (proportional to applied torque) and the shear rate (proportional to angular velocity) was measured. The reported viscosity (=shear stress/shear rate) at a certain shear stress was recorded after reaching a constant shear rate or after a maximum time of 2 min. The measurement was stopped when a shear rate of 1000 s-1 was exceeded.

Dry matter content was measured by keeping a sample in an oven at a temperature of 105° C. overnight (t=16 h) and by weighing the sample before and after it was kept in the oven. The weighing process was conducted following the standard ISO 4119/1995, "Determination of stock concentration", with the difference that the time was 16 h.

A turbidometric method based on nephelometry (90° angle between light source and detector) was used for measuring the turbidity of samples. HACH P2100 Turbidometer, with a 50 ml measuring vessel was used for turbidity measurements. The calibration of the apparatus was checked and controlled with standard calibration bottles/samples. The dry matter of the nanofibrillar cellulose sample was determined and 0.5 g of the sample, calculated as dry matter, was loaded in the measuring vessel, which was filled with tap water to 500 g and vigorously mixed by shaking for about 30 s. Without delay the aqueous mixture was divided into 5 measuring vessels, which were inserted in the turbidometer. Three measurements on each vessel were carried out. Mean value and standard deviation were calculated for each sample.

The properties of the native NFC hydrogel are shown in Table 1.

TABLE 1

The properties of the native nanofibrillar cellulose hydrogel obtained by 6, 8 or 10 rounds of fibrillation before and after autoclaving. Zero shear value has been determined as the highest point of the flow profile and the yield stress from the steepest tangent of the curve.

| | 6 rounds | | 8 rounds | | 10 rounds | |
|---|---|---|---|---|---|---|
| | Before | After | Before | After | Before | After |
| Dry matter | 1.12% | 1.16% | 1.11% | 1.14% | 1.11% | 1.13% |
| pH | 6.9 | 6.7 | 6.8 | 6.4 | 6.7 | 6.3 |
| Brookfield, 10 rpm (Pa·s) | 20.6 | 21.0 | 21.4 | — | 21.5 | 21.2 |
| Turbidity | 127 | 140 | 102 | 115 | 85 | 106 |
| Zero shear, 0.5% (Pa·s) | 1000 | 700 | 230 | 330 | 100 | 200 |
| Yield stress, 0.5% (Pa) | 1.3 | 2.2 | 1.5 | 2.0 | 1.0 | 1.8 |

Example 2—Aseptic Manufacturing of Nanocellulose Hydrogel

Bleached birch pulp was taken from a pulp mill after bleaching and after the final washing stage after bleaching at 4% dry solids content. The pulp mill did not use a biocide. Pulp was taken as aseptically as possible, so that the container was washed with ethanol and the person used clean gloves. The container was closed immediately after filling.

Nanocellulose was produced using a process that contained the following steps:
  washing the pulp to Nat-form by using alternated acid and alkaline steps, with washing in between;
  prerefining; and
  fluidization. The fluidization was conducted for 10 cycles.

All process steps were performed aseptically, so that the equipment was washed with ethanol or similar antimicrobial agent beforehand. The results of microbial cultivations are shown in Table 2.

TABLE 2

Microbial counts in the samples.

| | Aerobic bacteria | | Anaerobic bacteria | | Mold & yeast | |
|---|---|---|---|---|---|---|
| Sample | cfu/g | log (cfu/g) | cfu/g | log (cfu/g) | cfu/g | log (cfu/g) |
| Pulp from mill | 300 | 2.5 | <10 | <1 | 140 | 2.1 |
| Washed and prerefined | 100 | 2 | 50 | 1.7 | <10 | <1 |
| Fluidized | <10 | 1 | <10 | <1 | <10 | <1 |

It was noted that in each process step the microbial counts were smaller. Especially in the fluidization step the drop was at least 1 order of magnitude. The smallest number is indicated as "<10", because the samples were diluted in the measurement by a factor of 10. The smallest number of colonies that could be recorded is 1 cfu/g, and if there were fewer colonies, the colony count was <1 cfu/g. Because of the dilution, the number indicated was thus calculated as <10 cfu/g—in practice no growth was observed.

Example 3—Aseptic Manufacturing of Nanocellulose Hydrogel

The experiment was repeated using the same pulp as in Example 2. Microbial counts measured are shown in Table 3.

TABLE 3

Microbial counts in the samples.

| | Aerobic bacteria | | Anaerobic bacteria | | Mold & yeast | |
|---|---|---|---|---|---|---|
| Sample | cfu/g | log (cfu/g) | cfu/g | log (cfu/g) | cfu/g | log (cfu/g) |
| Pulp from mill | 300 | 2.5 | <10 | <1 | 140 | 2.1 |
| Washed and prerefined | <100 | 2 | 120 | 2.1 | 10 | <1 |
| Fluidized | 10 | 1 | <10 | <1 | 10 | <1 |

As compared to Example 2, the counts of anaerobic bacteria and mold & yeast appeared to be higher after prerefining, and after fluidization, aerobic bacteria and mold & yeast were present at a higher level. However, also in this experiment, compared to the microbial counts in the pulp, in each process step the colony counts decreased.

Example 4—Aseptic Manufacturing of Nanocellulose Hydrogel

Nanofibrillar cellulose hydrogel was prepared essentially as in Example 2. Samples were taken before and after fluidisator. Microbial counts were determined using a method based on modified SFS-EN ISO 8199. Microbial counts measured are shown in Table 4. The fluidisator treatment was capable of significantly reducing microbial counts.

TABLE 4

Microbial counts in the samples

| | Washed pulp | Fluidisator 1.2% 6 cycles |
|---|---|---|
| Aerobic bacteria, Petrifilm CFU/g | 5100 | 15 |
| Anaerobic bacteria, Petrifilm CFU/g | 0 | 10 |
| Aerobic fungi, Petrifilm CFU/g | 68 | 0 |
| Anaerobic fungi, Petrifilm CFU/g | 0 | 0 |

Example 5—Aseptic Manufacturing of Nanocellulose Hydrogel by Fluidization and UV Treatment Nanofibrillar cellulose hydrogel was prepared essentially as in Example 2 using 6 or 8 passes of fluidization. A week after the fluidization, the resulting hydrogel was subjected to a UV treatment, in which the hydrogel was spread on a Petri dish as a layer having a thickness of about 3.7 mm. The treatments were performed for a treatment time of at least 0.5 h so that the UV lamp was at a distance of 5 cm from the hydrogel. The UV radiation (UVC radiation) provided to the hydrogel sample was 0.25 W calculated on the basis of the dimensions of the hydrogel sample.

Samples were taken before and after the UV treatment. Microbial counts were determined using a method based on modified SFS-EN ISO 8199. Microbial counts measured are shown in Table 5. While the microbial counts were higher in the hydrogel after fluidization than in Example 4, due to the fact that the hydrogel was not immediately UV treated but stored for a week before the UV treatment, the UV treatment was capable of significantly reducing microbial counts.

TABLE 5

Microbial counts in the samples

| | Aerobic bacteria, Petrifilm CFU/g | Anaerobic bacteria, Petrifilm CFU/g | Aerobic fungi, Petrifilm CFU/g | Anaerobic fungi, Petrifilm CFU/g |
|---|---|---|---|---|
| Fluidisator 1.2% 8 passes, before UV | 9000 | 5400 | 0 | 0 |
| Fluidisator 1.2% 8 passes, after 0.5 h UV | 0 | 0 | 0 | 0 |
| Fluidisator 1.2% 6 passes, before UV | 370000 | 0 | 1300 | 0 |
| Fluidisator 1.2% 6 passes, after 0.5 h UV | 0 | 0 | 0 | 0 |

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A process for producing a nanofibrillar cellulose hydrogel, wherein the process comprises:
    obtaining bleached cellulose pulp fibers and providing an aqueous suspension thereof; and
    subjecting the cellulose pulp fibers in the aqueous suspension to at least 2 cycles of high pressure mechanical disintegration to obtain a nanofibrillar cellulose hydrogel and thereby reducing the number of viable microorganisms present in the suspension by a factor of at least $10^2$,
    wherein all steps of the process after obtaining the bleached cellulose pulp fibers are performed under conditions of ISO 8 of ISO 14644-1 cleanroom standards or stricter.

2. The process according to claim 1, wherein the process further comprises washing the cellulose pulp fibers with a sterile liquid prior to subjecting to the high pressure mechanical disintegration.

3. The process according to claim 1, wherein the process further comprises prerefining the cellulose pulp fibers to break down the cellulose pulp fibers prior to subjecting to the high pressure mechanical disintegration.

4. The process according to claim 1, wherein the high pressure mechanical disintegration is conducted using a pressure type homogenizer.

5. The process according to claim 1, further comprising subjecting the cellulose pulp fibers in the aqueous suspension to at least 2 cycles of high pressure mechanical disintegration to obtain a nanofibrillar cellulose hydrogel and thereby reducing the number of viable microorganisms present in the suspension by a factor of at least $10^3$.

6. The process according to claim 1, further comprising subjecting the cellulose pulp fibers in the aqueous suspension to 2 to 10 cycles of high pressure mechanical disintegration.

7. The process according to claim 1, wherein the process further comprises subjecting the nanofibrillar cellulose hydrogel to a further decontamination treatment for reducing the number of viable micro-organisms in the nanofibrillar cellulose hydrogel by a factor of at least $10^2$.

8. The process according to claim 7, wherein the further decontamination treatment comprises subjecting the nanofibrillar cellulose hydrogel to non-ionizing or ionizing radiation.

9. The process according to claim 7, wherein the further decontamination treatment comprises subjecting the nanofibrillar cellulose hydrogel to a heat treatment, wherein the heat treatment comprises keeping the nanofibrillar cellulose hydrogel at a temperature in the range of 72° C. to 100° C. for at least 15 seconds.

10. The process according to claim 7, wherein the further decontamination treatment comprises subjecting the nanofibrillar cellulose hydrogel to pulsed electric field processing.

11. The process according to claim 7, wherein the pH of the nanofibrillar cellulose hydrogel after the further decontamination treatment is at most 0.4 pH units lower than the pH of the nanofibrillar cellulose hydrogel before the further decontamination treatment.

12. The process according to claim 1, whereby a non-autoclaved nanofibrillar cellulose hydrogel that includes fewer than $10^{-1}$ CFU of a viable micro-organism for a unit of 1 gram of the nanofibrillar cellulose hydrogel is obtained.

13. The process according to claim 1, wherein the process further comprises maintaining conditions of ISO 5 of ISO 14644-1 cleanroom standards or stricter from the high pressure mechanical disintegration to packaging the nanofibrillar cellulose hydrogel.

14. The process according to claim 1, wherein the number of viable microorganisms is reduced during the process by a factor of at least $10^3$.

15. The process according to claim 1, wherein the nanofibrillar cellulose is native or anionic nanofibrillar cellulose.

16. The process of claim 1, wherein the consistency of the aqueous suspension subjected to the high pressure mechanical disintegration is at least 0.7% (w/w).

17. A method of producing nanofibrillar cellulose hydrogel, the method comprising:
    obtaining bleached cellulose pulp fibers directly from a pulp mill libertine, and providing an aqueous suspension thereof; and
    subjecting the cellulose pulp fibers in the aqueous suspension to at least 2 cycles of high pressure mechanical disintegration to obtain a nanofibrillar cellulose hydrogel, thereby reducing the number of viable microorganisms present in the suspension by a factor of at least $10^2$,
    wherein all steps of the process after obtaining the bleached cellulose pulp fibers are performed under conditions of ISO 8 of ISO 14644-1 cleanroom standards or stricter.

18. The method of claim 17, further comprising bleaching the cellulose pulp fibers in the pulp mill fiberline using an oxidizing process comprising acidic and alkaline conditions.

* * * * *

UNITED STATES PATENT AND TRADEMARK OFFICE
CERTIFICATE OF CORRECTION

PATENT NO. : 10,822,743 B2
APPLICATION NO. : 15/578778
DATED : November 3, 2020
INVENTOR(S) : Isko Kajanto et al.

Page 1 of 1

It is certified that error appears in the above-identified patent and that said Letters Patent is hereby corrected as shown below:

At Column 24, Line 51 (Claim 17, Line 4), please delete "libertine" and insert --fiberline-- therefor.

Signed and Sealed this
Fifth Day of January, 2021

Andrei Iancu
*Director of the United States Patent and Trademark Office*